United States Patent [19]
Banner et al.

[11] Patent Number: 6,102,868
[45] Date of Patent: Aug. 15, 2000

[54] METHOD AND SYSTEM FOR MEASURING THE CARDIAC OUTPUT OF A LIVING BEING

[75] Inventors: Michael J. Banner, Alachua; Jeffrey W. Skimming, Gainesville, both of Fla.

[73] Assignee: University of Florida, Gainesville, Fla.

[21] Appl. No.: 09/173,838

[22] Filed: Oct. 16, 1998

[51] Int. Cl.[7] .......................................... A61B 5/02
[52] U.S. Cl. .................... 600/484; 600/481; 600/526; 600/483
[58] Field of Search ................................ 600/481, 483, 600/484, 508, 526, 529, 532

[56] References Cited

U.S. PATENT DOCUMENTS

| | | |
|---|---|---|
| 4,909,259 | 3/1990 | Tehrani ................................. 600/526 |
| 4,949,724 | 8/1990 | Mahutte et al. ......................... 600/526 |
| 5,299,579 | 4/1994 | Gedeon et al. ......................... 600/526 |
| 5,836,300 | 11/1998 | Mault ..................................... 600/526 |

*Primary Examiner*—Cary O'Connor
*Assistant Examiner*—Navin Natnithithadha
*Attorney, Agent, or Firm*—Needle & Rosenberg, P.C.

[57] ABSTRACT

A system is provided for use in measuring the cardiac output of a living being. The system includes at least one sensor for measuring the lung carbon dioxide elimination rate of the living being and a processor for predicting the cardiac ouput level of the living being as a function of the current value of the lung carbon dioxide elimination rate based upon the predictive increase in cardiac output as the lung carbon dioxide elimination rate of the living being increases. Structure is provided for determining the cardiac ouput of an intubated living being and a non-intubated living being.

55 Claims, 9 Drawing Sheets

METHOD AND SYSTEM FOR MEASURING THE CARDIAC OUTPUT OF A LIVING BEING

BACKGROUND OF THE INVENTION

1. Field of the Invention

This invention generally relates to a method and system for monitoring the volumetric output of a heart, and more specifically, to a method and system for making this determination by using a non-invasive technique which monitors the carbon dioxide elimination rate of the patient.

2. Prior Art

Cardiac output, the volumetric rate at which blood is pumped through the heart, is one of the most important cardiovascular parameters. The cardiac output reflects the supply of oxygen and nutrients to the tissues of the patient. Measurements of cardiac output provide invaluable clinical information for quantifying the extent of cardiac dysfunction, indicating the optimal course of therapy, managing patient progress, and establishing check points for rehabilitation in a patient with a damaged or diseased heart, or one in whom fluid status control is essential. Exercise, as well as pathological conditions of the heart and circulatory system will alter cardiac output; therefore, the measurement of cardiac output is useful both in rehabilitation and critically ill patients.

Instrumentation currently in use for measurement of cardiac output has several disadvantages. Cardiac output may be measured either invasively or noninvasively. The most common invasive techniques are indicator dilution and thermal dilution.

The indicator dilution technique typically relies on the use of a dye or other indicator which is injected suddenly upstream of the heart and analyzed downstream of the heart. In the case of a dye, the density of dye in the blood increases initially to a maximum and then decays exponentially. The curve produced establishes an area under the curve indicative of the volume of blood pumped by the heart and the time taken for this blood to pass the point where analysis is being made. Of course before the density of the dye can taper off exponentially to substantially zero, recirculation of the dye will produce a second peak in the density curve introducing a distortion to the decaying exponential portion of the curve. This distortion cannot be tolerated if an accurate reading of cardiac output is to be established. Various methods have been proposed to compensate for the distortion but these compensation methods have been found to be impractical due to a combination of excessive time required for calculating the compensation and the uncertainty in the reading of the cardiac output due to the inaccuracy of the applied approximation methods. The use of indicator dilution techniques are disclosed, for example, in U.S. Pat. No. 4,572,206 to Greddes et al.; U.S. Pat. No. 4,380,237 to Newbower; and U.S. Pat. No. 4,015,593 to Elings et al.

The thermal dilution technique relies on the use of a chilled thermal indicator that is introduced into the right atrium of the heart. The thermal indicator is then carried by the blood through the heart to the pulmonary artery. As theThe thermal indicator mixed with surrounding blood in the heart, it cools the temperature of the blood before the blood is pumped out of the heart and passes a thermistor. The thermistor measures the decrease in the blood temperature as the blood flows pasts the thermistor in the pulmonary artery. The time-temperature information derived from the thermistor is then used to calculate the cardiac output of the patient. The use of thermal dilution techniques are disclosed, for example, in U.S. Pat. No. 5,595,181 to Hubbard; U.S. Pat. No. 5,285,796 to Hughes; and U.S. Pat. No. 4,819,655 to Webler.

These invasive techniques present three primary disadvantages. First, the techniques require the insertion of catheter into the patients body. Normally, the catheter is inserted in the femoral artery and threaded into the heart. Since these invasive techniques for measuring cardiac output involve penetration of the skin by a catheter, they present an inherent undesirable risk of trauma and infection to the patient. Second, these techniques require the use of complex instrumentation which must be operated by skilled personnel. Finally, these techniques allow only intermittent measurement of the cardiac output since it is possible to obtain only one determination of cardiac output per injection.

The noninvasive techniques for measuring cardiac parameters include ballistocardiograpy, electrical impedance measurements, ultrasonics, phonocardiography, and vibrocardiography. The instrumentation typically involved in present noninvasive techniques for measuring cardiac output is complex, expensive, inconvenient to use and requires highly trained operators. The most common noninvasive technique is the measurement of the cardiovascular impedance change during a systolic downstroke. Such techniques are disclosed, for example, in U.S. Pat. No. 5,423,326 to Wang et al.; U.S. Pat. No. 4,898,176 to Petre; U.S. Pat. No. 4,947,852 to Nassi et al.; and U.S. Pat. No. 4,450,527 to Sramek. The models used in such electrical impedance techniques generally incorporate many simplifying assumptions which, depending upon the divergence of an actual living body form the assumed conditions of the model, may degrade the accuracy of these methods significantly.

Still other methods of cardiac output measurement are based upon the Fick principle. According to this principle, the rate of uptake or release of a substance to or from blood at the lung is equal to the blood flow past the lung and the content difference of the substance at each side of the lung. This can be expressed by the equation:

$$\text{Uptake} = Q(c_2 - c_1),$$

where Q is the blood flow (cardiac output), $c_2$ is the content of the substance leaving from the lung and $c_1$ is the content of the substance coming to the lung. Applying the relationship to carbon dioxide yields:

$$Q = VCO_2 / (c_v CO_2 - c_a CO_2),$$

where $VCO_2$ is the volume of carbon dioxide produced by the patient per unit time and $c_v CO_2$ and $c_a CO_2$ are the mixed venous and arterial carbon dioxide contents. Determination of $VCO_2$ requires a volume measurement (e.g., via intergration of a flow signal or via a rotameter) and a fractional concentration measurment (e.g., via mass spectrometer or gas analyzer (infrared or polarographic)). This method for determining cardiac output unfortunately retains still presents the inherent disadvantages associated with the previously mentioned invasive methods as a pulmonary catheter is required to be inserted into the patient's heart to monitor the mixed venous oxygen saturation of the blood. An example of this method is disclosed in U.S. Pat. No. 4,949,724 to Mahutte, et al.

The Fick method has also been applied to carbon dioxide employing equation to obtain intermittent cardiac output. The $c_v CO_2$ is usually estimated from the partial pressure of carbon dioxide ($P_v CO_2$) which is typically obtained indirectly by rebreathing. Such methods are described in Davis, C.C., et al., *Measurements of Cardiac Output in Seriously Ill*

*Patients using a CO Rebreathing Method*, Chest 73, 167, 1978; and Blanch, et al., *Accuracy of an Indirect Carbon Dioxide Fick* Method in Determination of the Cardiac Output in Critically Ill Mechanically Ventilated Patients, Int. Care Med 14, 131, 1988. A major disadvantage of this method is that it yields only intermittent cardiac output values since the partial pressure of carbon dioxide is estimated via rebreathing.

These prior art invasive and noninvasive techniques, detailed above, require great skill in application, carry inherent risks to the patient, and have degraded accuracy. Thus there still remains a need for a noninvasive technique that simply and easily determines cardiac output.

SUMMARY OF THE INVENTION

The present invention results from the discovery that there is a strong correlation between the cardiac output of a living being and the volume of carbon dioxide per unit time expired by the patient, i.e. the lung carbon dioxide elimination rate. The principle object of the present invention is to provide a simple and easy method and corresponding system for obtaining noninvasively a measurement of cardiac output.

Another object of the invention is to provide a noninvasive method and system for accurately predicting the cardiac output level of the patient based on maximizing the correlation between readily measured exhalation gas parameters and directly measured cardiac output.

The present invention is directed to a method and system for predicting the cardiac ouput level from a patient. The volume of carbon dioxide expired by the patient, i.e. the lung carbon dioxide elimination rate, is continuously monitored and the predicted cardiac output level of the patient is calculated in real time from the current monitored value of the lung carbon dioxide elimination rate and the application of a predictive relationship. The predictive relationship correlates the cardiac output level of the patient as a function of the current value of the lung carbon dioxide elimination rate. A first predictive relationship exists for patient with a substantially abnormal ventilation-to-perfusion ratio (an "ill" patient) or a second predictive relationship exists for a patient with a substantially normal ventilation-to-perfusion ratio (a "healthy" patient).

In one preferred embodiment, the present method and system allows the operator to input a selection of either the first or second predictive relationships so that the appropriate predictive relationship may be selectively chosen for the accurate prediction of the cardiac output level of the patient based upon the relative respiratory health of the patient.

Preferably, in order to determine the required current value of the lung carbon dioxide elimination rate of the patient, a flow rate sensor and a carbon dioxide level sensor are provided. The flow rate sensor and the carbon dioxide level sensor are preferably placed in a flow path of the exhaled gas near the proximal end of a patient breathing attachment which is in fluid/flow communication with the lung of the patient. Data, indicative of the measured volume of the gas expired by the patient, is extracted from the flow rate data provided by the flow rate sensor and a set of curve data, representative of the sensed carbon dioxide level of the exhaled gas as a function of the measured volume of the expired gas, is stored. The set of curve data is subsequently integrated to determine the current value of the lung carbon dioxide elimination rate.

The predicted cardiac output level of the patient is displayed to the operator for medical diagnosis of the patient's condition. Thus, the present invention provides significant improvements in the real time noninvasive measurement of the cardiac output level of the patient based upon the readily determined lung carbon dioxide elimination rate of the patient.

DETAILED DESCRIPTION OF THE PREFERRED EMBODIMENT

Figure 1:
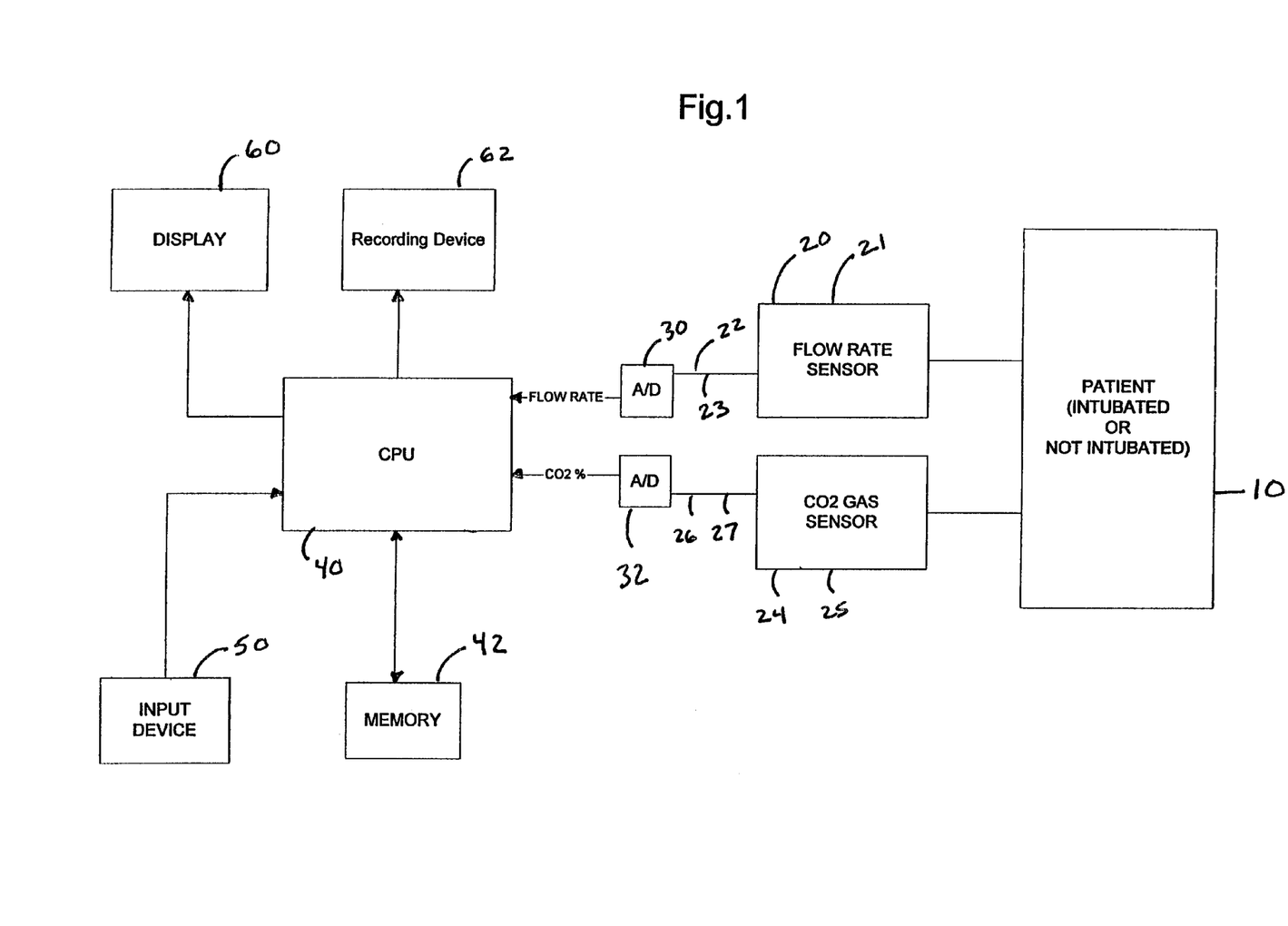
FIG. 1 is a block diagram of a preferred embodiment of the present invention of a system for noninvasively determining the cardiac output of a living being.
Figure 2:
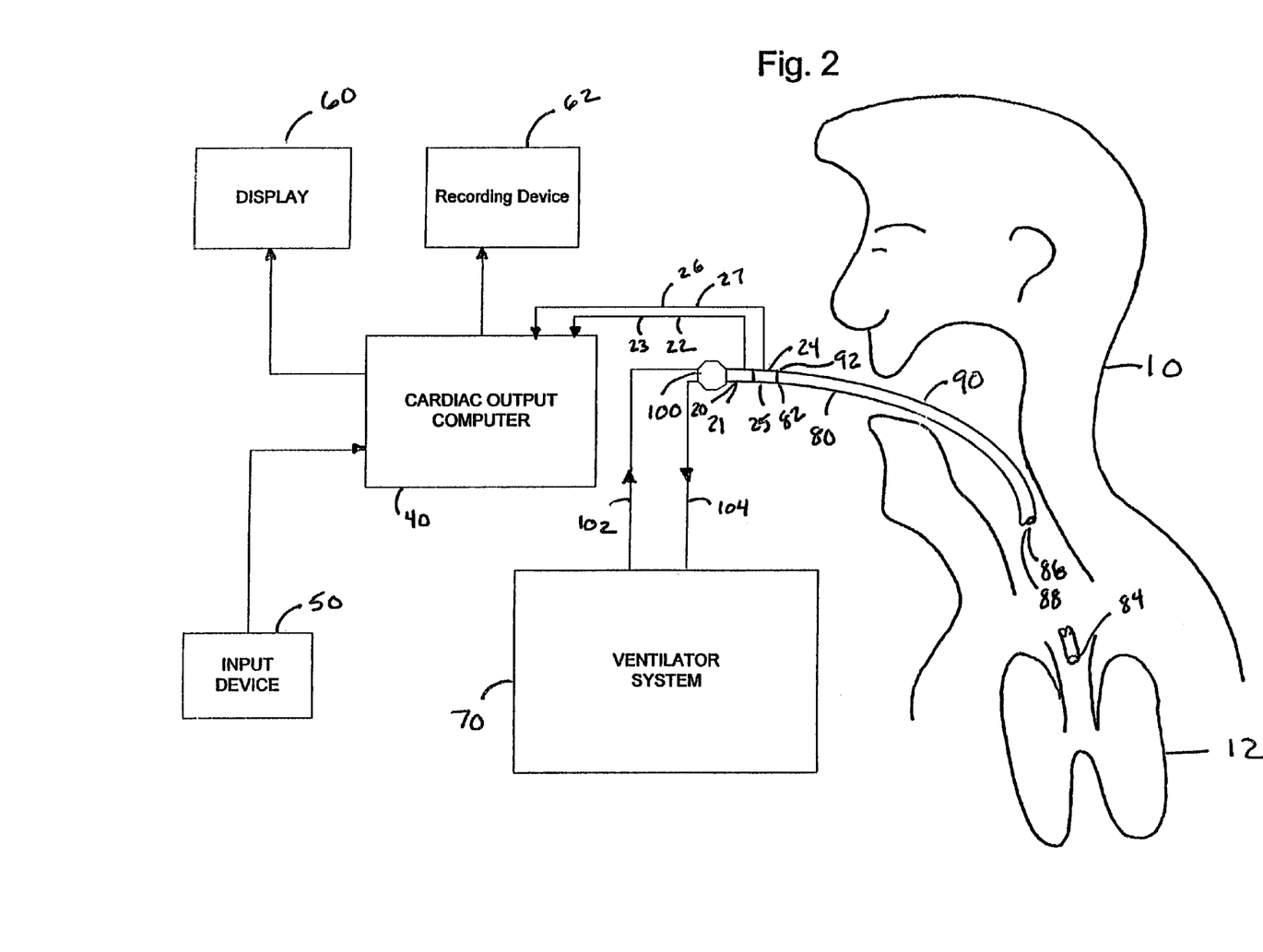
FIG. 2 illustrates the preferred embodiment of the present invention in use, showing the flow rate measuring means and carbon dioxide sensing means disposed in the flow path of the gas expired by the living being that has been intubated with a patient breathing attachment.
Figure 3:
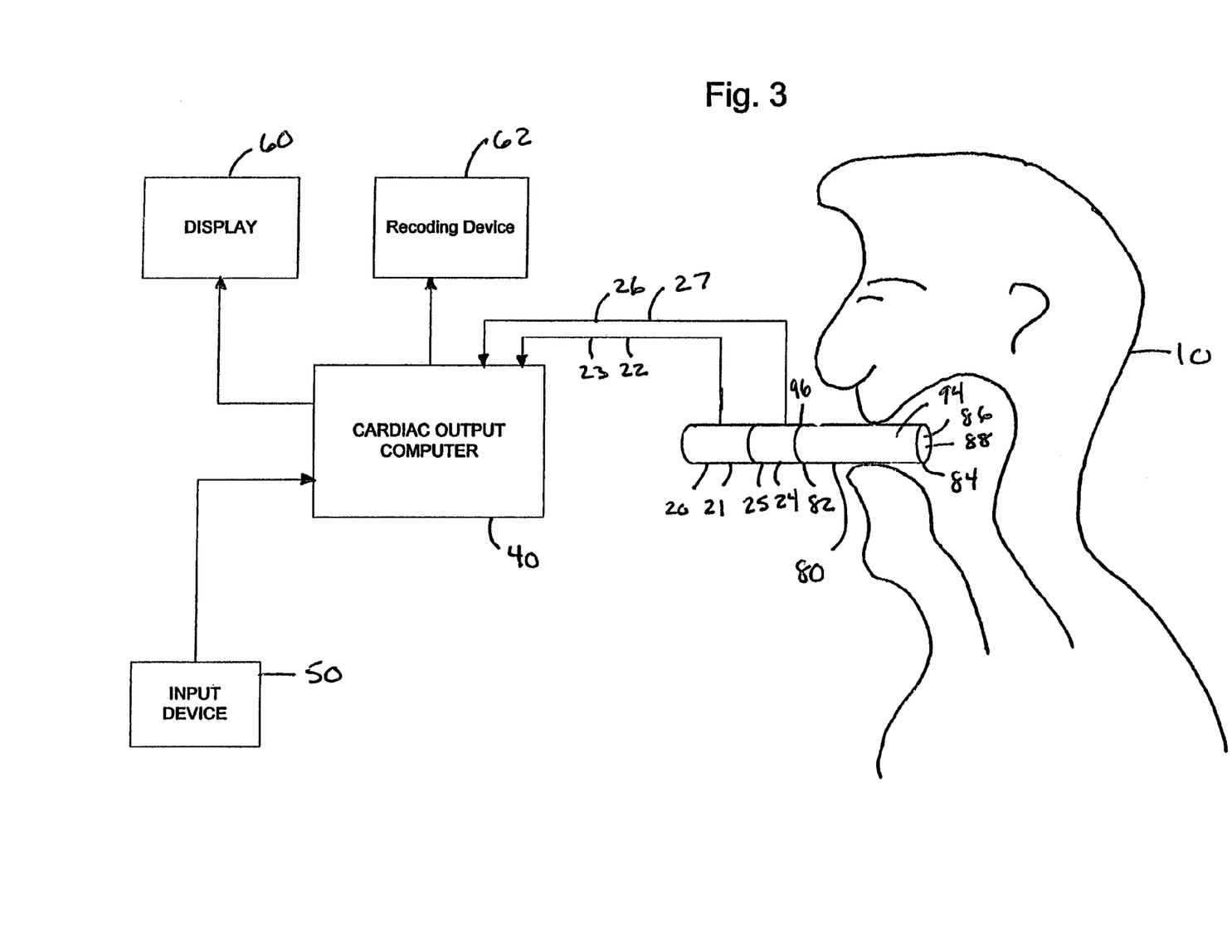
FIG. 3 illustrates the preferred embodiment of the present invention in use, showing the flow rate measuring means and the carbon dioxide sensing means disposed in the flow path of the gas expired by the living being that has not been intubated with a patient breathing attachment.

Referring to FIGS. 1–4, a patient is indicated at 10. Various continuous monitoring devices are coupled to the patient to facilitate the continuous cardiac output measurement of the present invention. Each of these devices are commercially available. As shown in FIGS. 1–3, in the preferred embodiment of the present invention, two electrical sensors are disposed in the flow path of the gas expired by the patient to obtain the signals used by the present invention to determine the cardiac output of the patient. The first electrical sensor 20 is preferably a flow rate measuring sensor 21 that measures the flow rate of the gas expired by the patient during the exhalation effort. The flow rate measuring sensor 21 is preferably a differential pressure analyzer, such as pneumotachometer, which generates a flow signal 22 that is representative of the flow rate of the gas expired by the patient during an exhalation effort per unit time (L/min). This flow signal 21 is delivered via line 23 to a processor unit 40. The flow rate measuring sensor 21 may, for example, be comprised of a disposable, variable orifice pneumotachometer provided by Accutach, Glen Medical Products or a fixed orifice differential pressure pneumotach by Novametric Medical Systems. However, it must be noted that any sensor 20 capable of sensing the flow rate of the gas expired by the patient and providing a signal representative of that flow rate could be substituted for the differential pressure analyzer. A rotameter could be a suitable substitute.

The second electrical sensor 24 is preferably a carbon dioxide analyzer 25 that senses the carbon dioxide level in the gas expired by the patient during the exhalation effort. Any sensor 24 that is capable of determining the fractional composition of carbon dioxide expired by the patient in an exhalation effort and providing a signal representative of that fractional composition of carbon dioxide may be substituted for the carbon dioxide analyzer 25. A mass spectrometer or a infrared or polarograpic gas analyzer might be suitable alternatives. Preferably however, the carbon dioxide analyzer 25 is a capnometer, of a type known to one skilled in the art, either aspirating or nonaspirating, which generates a carbon dioxide signal 26 that is representative of the fractional composition of the carbon dioxide in the gas expired by the patient during the exhalation effort (% $CO_2$). More particularly, it is preferred that the carbon dioxide analyzer 25 be an aspirating, or mainstream, infrared capnometer. The carbon dioxide signal 26 is delivered via line 27 to the processor unit 40. For example, the carbon dioxide analyzer 25 may be comprised of a mainstream, infrared capnometer supplied by Capnogard, 1265, Novametrix Medical Systems.

The patient 10 is preferably provided with a breathing attachment 80 that has a proximal end 82, an opposed distal end 84, and defines a breathing channel 86 extending therethrough between the proximal and distal ends 82, 84. As shown in FIGS. 2 and 3, the distal end 84 of the breathing attachment 80 is in fluid communication with the lung 12 of the patient 10 and defines a flow path 88 for the gas, i.e. within the breathing channel 86, expired by the patient 10. The breathing attachment 80 therefore provides a convenient structure for attachment of the first and second electrical sensors 20, 24. However, no particular form of breathing attachment 80 is required to be used in the present invention. Rather, any form that allow the measurement of the flow rate, or the volume, of the exhaled gas and the fractional concentration of carbon dioxide present in the gas expired by the patient 10 in an exhalation effort is acceptable for the present invention.

For example, as shown in FIG. 2, the patient may be intubated with a breathing attachment 80 in the form of an endotracheal tube 90. A standard commercially available disposable endotracheal tube 90 may be used. In commercial medical ventilators common to one skilled in the art, if the patient 10 is being ventilated, the endotracheal tube 90 is normally connected to a wye fitting 100 which is in turn connected to the inhalation limb 102 and the exhalation limb 104 of the medical ventilator 70. The first and second electrical sensors 20, 24 may be applied anywhere on the endotracheal tube 90 or the exhalation limb 104 of the ventilator 70. However, for heightened accuracy of the cardiac output level measurement, it is preferred that the first and second electrical sensors 20, 24 be attached to the breathing attachment 80, i.e. the endotracheal tube 90 in this example, such that the first and second electrical sensors 20,24 are disposed in the flow path 88 of the exhaled gas. More particularly, it is preferred that the first and second sensors 20, 24 be attached to the proximal end 82 of the breathing attachment 80 so that the sensors 20, 24 are positioned in series between the end of the endotracheal tube 90 and the wye fitting 100 of the medical ventilator 70. The first and second electrical sensors 20, 24 may be attached to the endotracheal tube 90 in any order.

Attaching the first and second sensors 20, 24 to the proximal end 92 of the endotracheal tube 90 allows for the uncomplicated attachment of the first and second sensors 20, 22 to the end of the endotracheal tube 90 so that the sensors are disposed in the flow path 88 of the gas expired by the patient 10. Further, this configuration of the sensors 20, 24 allows for the use of a standard disposable endotracheal tube 90 since no physical modification to the endotracheal tube 90 are necessitated in order to dispose the sensors 20, 24 in the flow path 88 of the gas. Therefore, the expense of calculating the cardiac output level of the patient is minimized as common inexpensive disposable endotracheal tubes 90 may be utilized in the present invention.

Alternatively, as shown in FIG. 3, the patient breathing attachment 80 may consist of a simple disposable breathing tube structure 94. In this example, the first and second electrical sensors 20, 24 may be attached anywhere on the breathing tube 94. The only requirement is that the sensors 20, 24 be disposed in the flow path 88 of the exhaled gas. More particularly however, it is preferred that the first and second sensors 20, 24 be attached to the proximal end 82 of the breathing attachment 80, i.e. the breathing tube 94 of this example, so that the sensors 20, 24 are positioned in series at the proximal end 96 of the breathing tube 94. This allows for the use of an inexpensive disposable breathing tube structure 94 as no physical modification to the breathing tube 94 are required to accommodate the first and second electrical sensors 20, 24.

Figure 4:
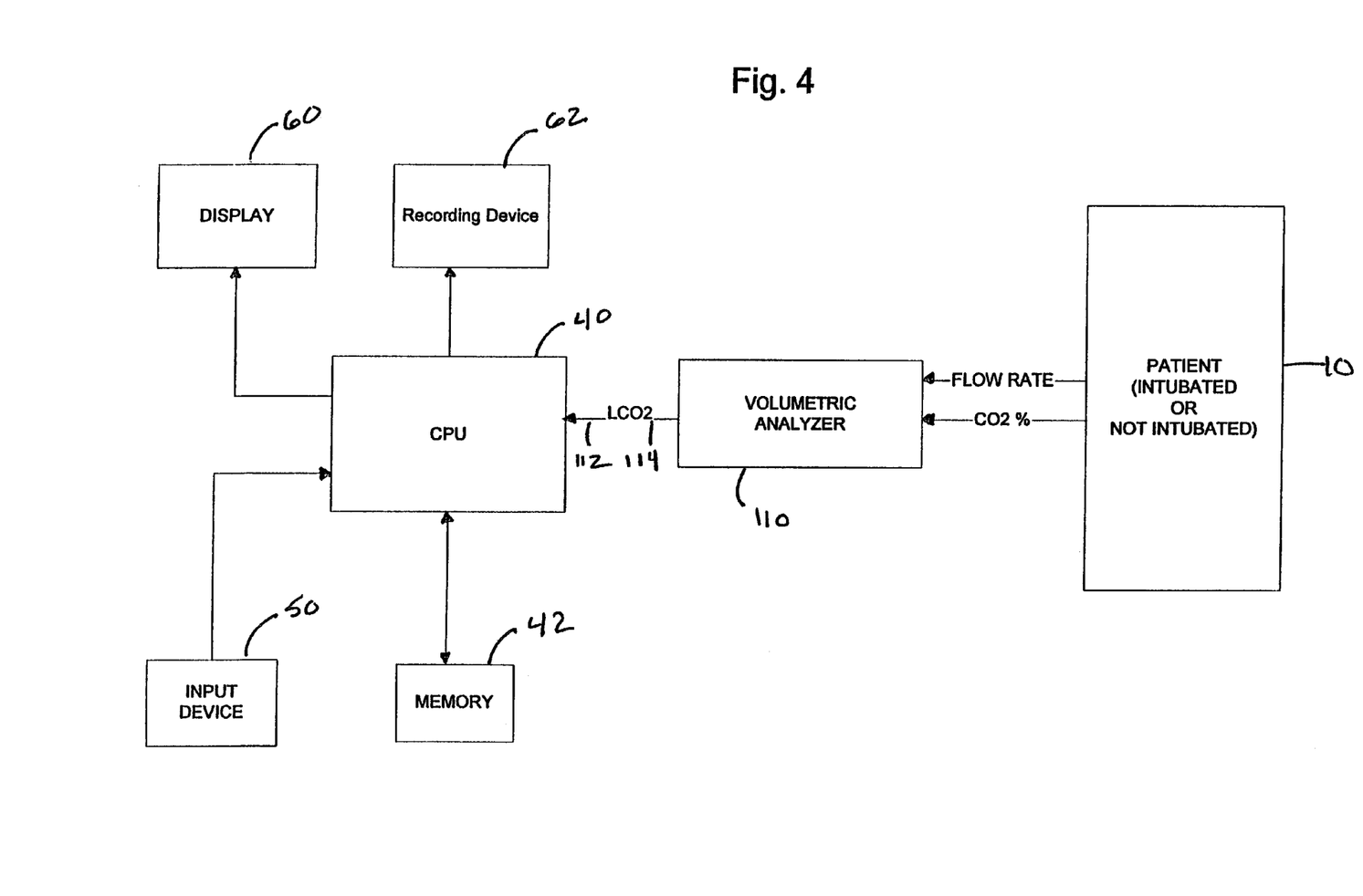
FIG. 4 is a block diagram of an alternate embodiment of the present invention of a system for noninvasively determining the cardiac output of a living being, showing a volumetric analyzer means for determining the lung carbon dioxide elimination rate and for generating a lung carbon dioxide elimination rate output signal.

Referring now to the alternative embodiment of the present invention shown in FIG. 4, the volume of the carbon dioxide expired by the patient may also be continuously monitored by means of an integrated volumetric analyzer 110 which includes the flow rate monitoring sensor 21 and the carbon dioxide sensor 25, for example the pneumotachometer and capnometer described above, along with appropriate processing circuitry. A volumetric output signal 112 is provided which is representative of the volume of carbon dioxide expired by the patient per unit time (e.g., ml/min). The volumetric analyzer 110 may, for example, be comprised of a Beckman MMC Horizon system which provides a volumetric output signal 112 representative of lung carbon dioxide elimination rate in ml/min. Such a volumetric output signal 112 is also provided by a Waters Instruments, Inc. MRM-6000 metabolic analyzer or a Novametric Medical Systems volumetric carbon dioxide analyzer. In this embodiment, the volumetric output signal 112 is delivered via line 114 to the processor 40.

Referring to FIGS. 1–3, the processor 40 may be any device for processing flow signals 22 and carbon dioxide signals 26 to determine a current value of the patient lung carbon dioxide elimination rate and for correlating the current value to the cardiac output level of the patient thereby predicting the current cardiac output level of the patient 10. Alternatively, as shown in FIG. 4, if the volumetric analyzer 110 having its own processing circuitry is used, the processor 40 may be any device for processing volumetric output signals 112, which is representative of the current value of the lung carbon dioxide elimination rate of the patient, to correlate the current value to the cardiac output level of the patient 10. The processor 40 may be analog or digital and should contain circuits to be programmed for performing mathematical functions such as waveform averaging, amplification, linearization, signal rejection, differentiation, intergration, addition, subtraction and multiplication, where desired. Circuits or programs for performing these functions are conventional and well known, and they form no part of the present invention.

Analog to digital converters must be provided in a digital environment for digital value sampling of otherwise analog signals. For example, a first analog-to-digital converter 30 may be coupled to the flow rate sensor 21 if conversion of the flow signal 22 is required. Similarly, if conversion of the carbon dioxide signal 26 is required, a second analog-to-digital converter 32 should be coupled to the carbon dioxide sensor 25. Thus, if required, the flow signal 22 and/or the carbon dioxide signal 26 from the respective sensors 21, 25 are continuously converted to digital signals by the converters 30, 32 prior to the use by the processor 40 or by the processing circuitry of the volumetric analyzer 110.

In many cases, the preferred processor 40 may be a microcomputer programmed to accomplish the necessary signal processing functions and prediction function and to deliver the determined cardiac output value via line to a display 60, such as a CRT monitor, and/or via line to a permanent recording device 62, such as a printer and/or a plotter. A microcomputer has the advantage over dedicated analog or digital processors in that it has the flexibility to be programmed to store and analyze data and to provide hard copy in many different forms.

Further, the processor 40 may have an input device 50 which, in the preferred embodiment, is a membrane keypad, a keyboard, or other suitable input device. An operator of the system may provide the processor 40 with any number of desirable input parameters, such as patient identification information, patient age, patient weight, patient health (healthy indicating that the patient has a substantially normal ventilationto-perfusion relationship and ill indicating that the patient has a substantially abnormal ventilation-to-perfusion relationship), or any other desired patient statistics.

Thus, in the preferred embodiment, the processor 40 receives continuous signals 22, 26 indicating the current value of the flow rate of gas expired by the patient during an exhalation effort of the patient (continuously converted to a digital signal if the processor design requires a digital signal and the flow signal 22 generated from the flow rate measuring sensor 21 is an analog signal) and the current value of the carbon dioxide level of gas expired by the patient during an exhalation effort of the patient (continuously converted to a digital signal if the processor design requires a digital signal and the carbon dioxide level signal 26 generated from the carbon dioxide sensor 25 is an analog signal). And, in the alternative embodiment of the present invention using a volumetric analyzer 110, the processor 40 receives continuous signals indicating the current value of the lung carbon dioxide elimination rate.

Figure 5:
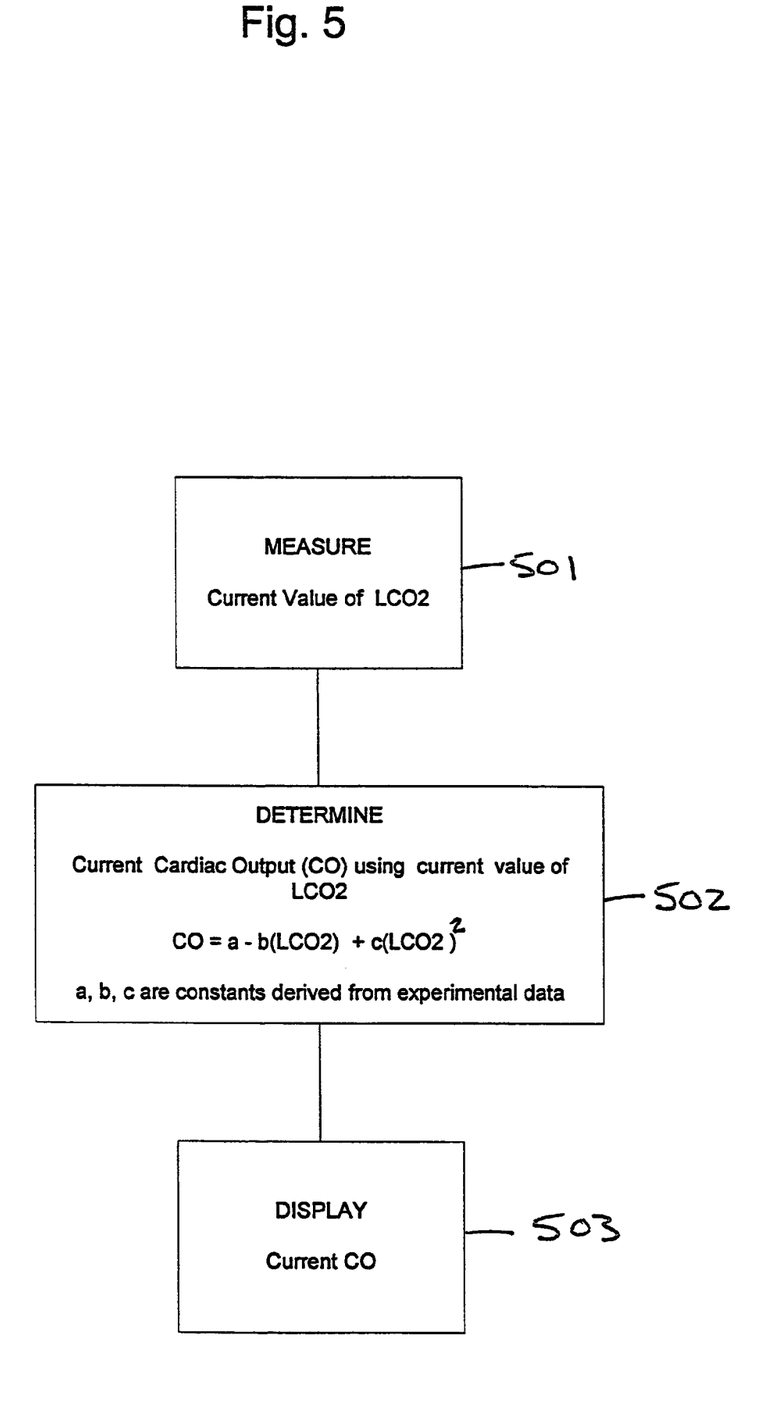
FIG. 5 is a block diagram illustrating the method of the present invention.
Figure 6:
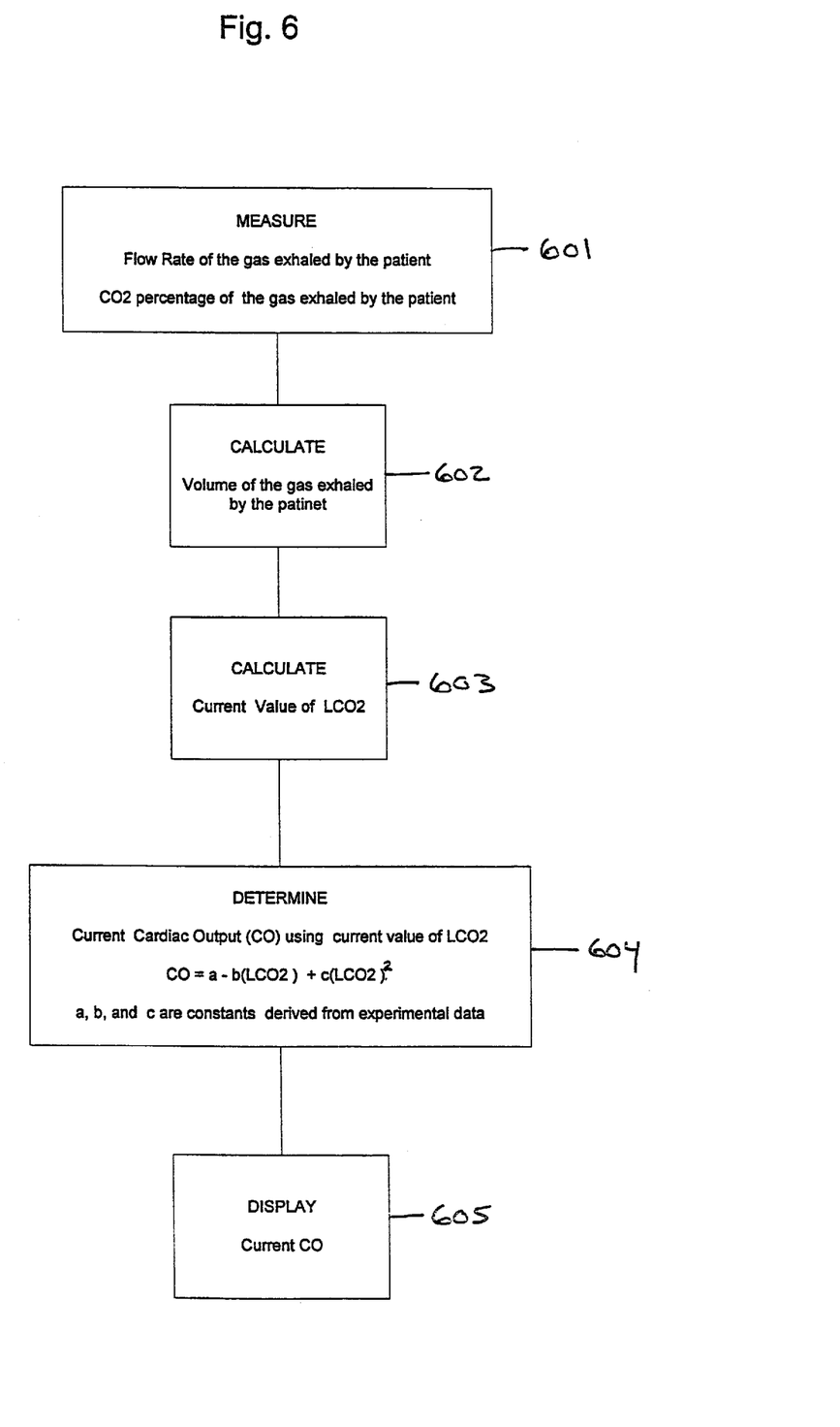
FIG. 6 is a block diagram illustrating the method of the present invention wherein a flow sensor means and a carbon dioxide level sensing means are used to determine the current value of the lung carbon dioxide elimination rate.
Figure 7:
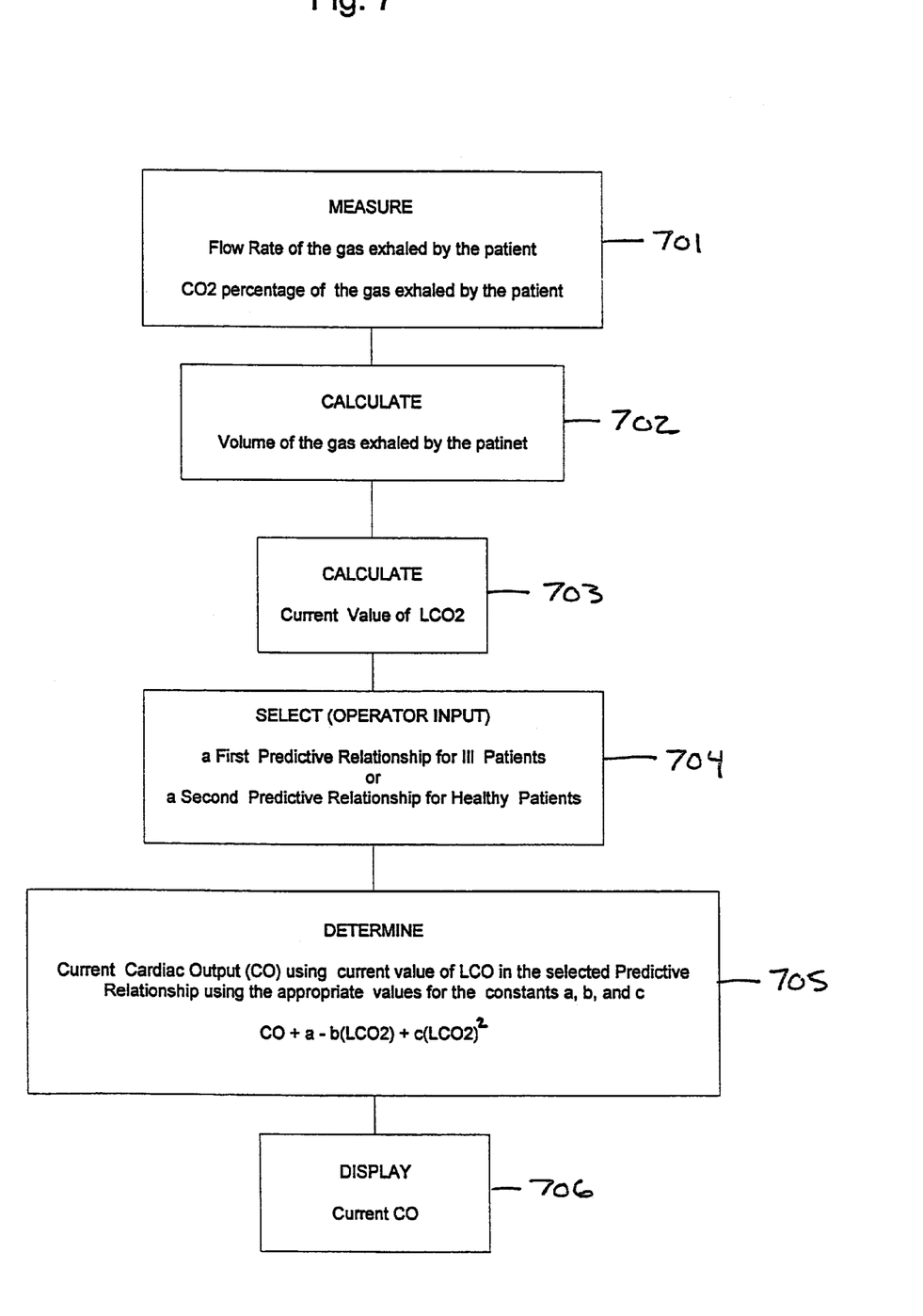
FIG. 7 is a block diagram illustrating the method of the preferred embodiment of the present invention wherein a predictive relationship, dependent upon the relative respiratory health of the patient, is selected for the determination of the cardiac ouput level.

The method for continuously measuring the cardiac level of the patient with the system of the present invention is illustrated in FIGS. 5–7. First, the flow rate measurement sensor 21 and the carbon dioxide sensor 25 are positioned so that they are disposed in the flow path 88 of the gas expired by the patient 10. Preferably, the patient 10 is breathing into a breathing attachment 80 so that the sensors may be conveniently applied to the breathing attachment as described above. Next, the measurement process is started by enabling the processor 40. When the measurement process is started, in Blocks 601 and 701, the flow rate measuring sensor 21 continuously measures the flow rate of the exhaled gas expired by the patient 10 and generates a flow signal 22 which is transmitted toward the processor 40. If required, the flow signal 21 is then continuously digitized by an analog-to-digital converter 30 operating at an appropriate sampling frequency. The digitized flow signal 21 is then passed, for a predetermined time delay, to the processor's memory 42 for storage prior to further processing. Referring to Blocks 602 and 702, the flow rate data is replaced with data generated by intergration. The resulting integrated data is representative of the measured volume of the exhaled gas.

In Blocks 601 and 701, concurrent with the measurement of the flow rate of the as expired by the patient during the exhalation effort, the carbon dioxide sensor 25 continuously senses the carbon dioxide level, i.e., the percentage of carbon dioxide present in the exhaled gas, of the exhaled gas expired by the patient and generates a carbon dioxide signal 26 which is transmitted toward the processor 40. If required, the carbon dioxide signal 26 is then continuously digitized by an analog-to-digital converter 32 operating at an appropriate sampling frequency. The digitized carbon dioxide signal 26 is then passed, for a predetermined time delay, to the processor's memory 42 for storage prior to further processing.

Subsequently, referring to Blocks 501, 603 and 703, a set of curve data representative of the sensed carbon dioxide level of the exhaled gas as a function of the measured exhaled volume of the gas is plotted and passed to the processor's memory 42 for storage prior to further processing. The set of curve data is then replaced with data generated by integrating. The resulting integrated data is representative of the current value of the patient lung carbon dioxide elimination rate and is stored in the processor's memory 42 for future use.

As shown in FIG. 5, in Block 501 all of the above steps of the method of the present invention regarding the measurement and sensing of the flow rate and carbon dioxide level and the processing of the lung carbon dioxide elimination rate from the flow rate and carbon dioxide data may be accomplished by a volumetric analyzer 110, as described above, having the appropriate processing circuitry. Such a volumetric analyzer 110 would transmit a volumetric signal 112 to the processor 40 representative of the lung carbon dioxide elimination rate of the patient.

Referring now to FIGS. 5–7 and Block 501, 603 and 703, the measurement of the lung carbon dioxide elimination rate may be generated using a single breath carbon dioxide method, known to one skilled in the art, using only a single breath to calculate the patient lung carbon dioxide elimination rate, or, preferably, by using the single breath carbon dioxide method and averaging the measurement of volumetric lung carbon dioxide over time intervals to provide an accurate representation of the lung carbon dioxide elimination rate produced by the patient. The time interval may be any predetermined time interval, however, it is preferred that the time interval be one minute. This allows for a continually updated current value of lung carbon dioxide elimination rate. The data points representative of the current value of the lung carbon dioxide elimination rate are preferably associated in the memory 42 of the processor 40 with other parameters inputted by the operator, such as patient identification, date, time, and other patient parameters, such as whether the patient is healthy, with a normal ventilation-to-perfusion relationship, or ill, with an abnormal ventilation-to-perfusion relationship.

Through the discovery that there is a highly predictive relationship between an increasing value of the lung carbon dioxide elimination rate and a corresponding increase in the cardiac output of the patient 10, the resultant current value of the lung carbon dioxide elimination rate may then correlated to the cardiac output level of the patient, as shown in Blocks 502, 604 and 705, by applying the following predictive relationship:

$$CO = a - b(LCO_2) + c(LCO_2)^2$$

where CO is the cardiac output level of the patient in L/min, $LCO_2$ is the current value of the lung carbon dioxide elimination rate of the patient in ml/min, and a, b, and c are constants dependent upon experimental data. In Block 503, 605 and 706, the cardiac output level may then be recorded on a hard copy device such as a printer or may be visually displayed to the operator. The cardiac output level may also be stored in the memory 42 of the processor 40 for future use.

As mentioned above, the present invention results from the discovery that the current lung carbon dioxide elimination rate, i.e., the volume of carbon dioxide expired by the patient per unit time, present a strong correlation to the cardiac output of the patient 10. This discovery resulted from statistical analyses of the correlation between the lung carbon dioxide elimination rate of the patient on one hand, and the cardiac output measurements obtained by conventional invasive thermal dilution techniques, on the other hand. This statistical analysis was accomplished for both of healthy and seriously ill patients.

Eleven adults with respiratory failure and abnormal ventilation-to-perfusion relationships were studied. Twenty-one adults without respiratory complaint and with normal ventilation-to-perfusion relationships were also studied. All patients were intubated, mechanically ventilated, and had pulmonary artery and arterial catheters placed. Data from a mainstream flow measurement sensor and an infrared capnograph sensor for sensing the percentage of carbon dioxide exhaled by the patient, positioned between the endotracheal tube and the wye piece of the ventilator system, were directed to a processor such as illustrated in FIG. 1 for determination of the lung carbon dioxide elimination rate simultaneously with scheduled cardiac measurements using cold saline injections in accordance with the conventional thermal dilution technique.

The following data were developed for each set of measurements:

FR: The flow rate of the gas exhaled by the patient.

$CO_2$: The percentage of carbon dioxide present in the gas exhaled by the patient.

$LCO_2$: The patient's lung carbon dioxide elimination rate.

CO: The cardiac output level of the patient.

Figure 8:
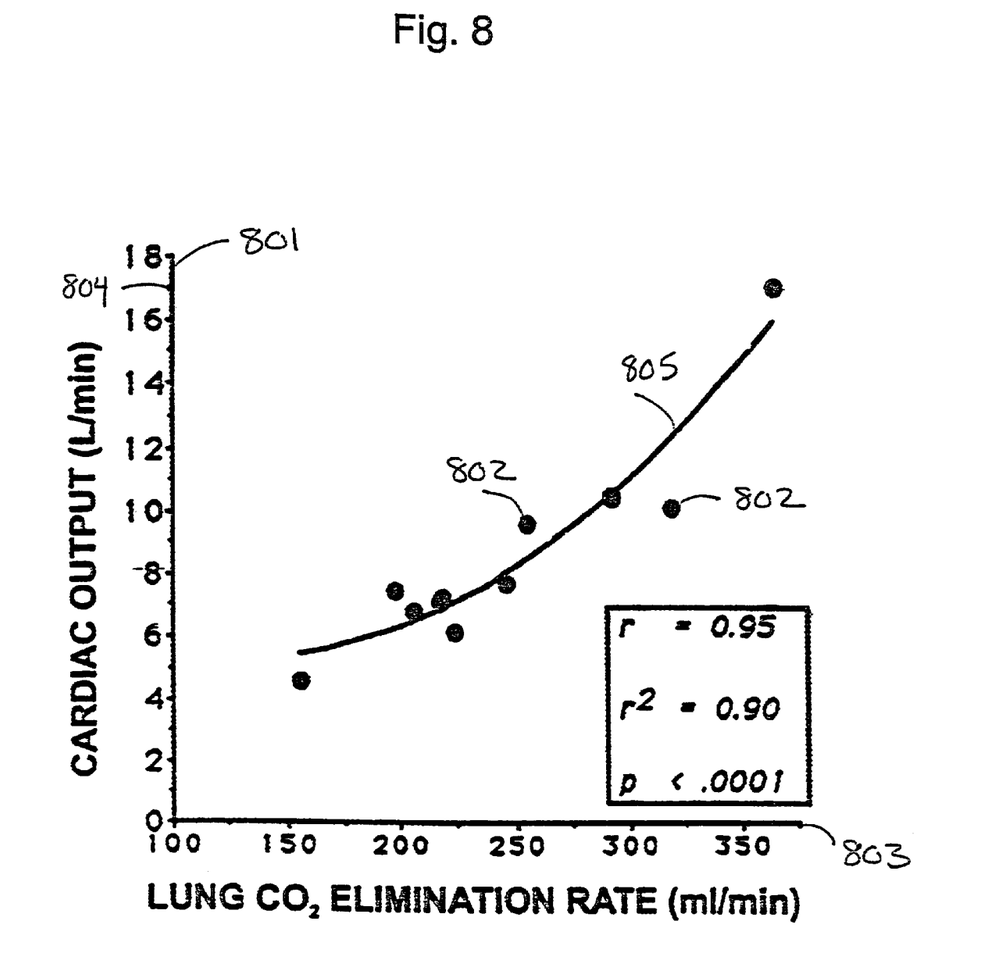
FIG. 8 is a lung carbon dioxide elimination rate-cardiac output curve illustrating the correlation between lung carbon dioxide elimination rate and cardiac output for a critically ill patient.

The results of a correlation analysis of $LCO_2$ and CO for each of the measure sets of data surprisingly showed a positive and significant correlation between $LCO_2$ and CO. The regression analysis fields the following predictive polynomial relationship:

$$CO = a - b(LCO_2) + c(LCO_2)^2$$

where CO is the cardiac output level of the patient in L/min, $LCO_2$ is the current value of the lung carbon dioxide elimination rate of the patient in ml/min, and a, b, and c are constants, the value of which depends upon the experimental data. For example, referring to the experimental plot 801 illustrated in FIG. 8, the experimental data points 902 representative of the eleven measurements taken on the patients with abnormal ventilation-to-perfusion relationships, using lung carbon dioxide elimination rates derived from single breath analysis taken over a one minute time interval of patient respiration, are shown against an x-axis 803 representative of lung carbon dioxide elimination rate (ml/min) and a y-axis 804 representative of cardiac output (L/min). Statistical analysis yielded curve 805 having the constant values for a first predictive relationship for ill patients of:

a=8.026;

b=0.045; and c=0.00018415.

Figure 9:
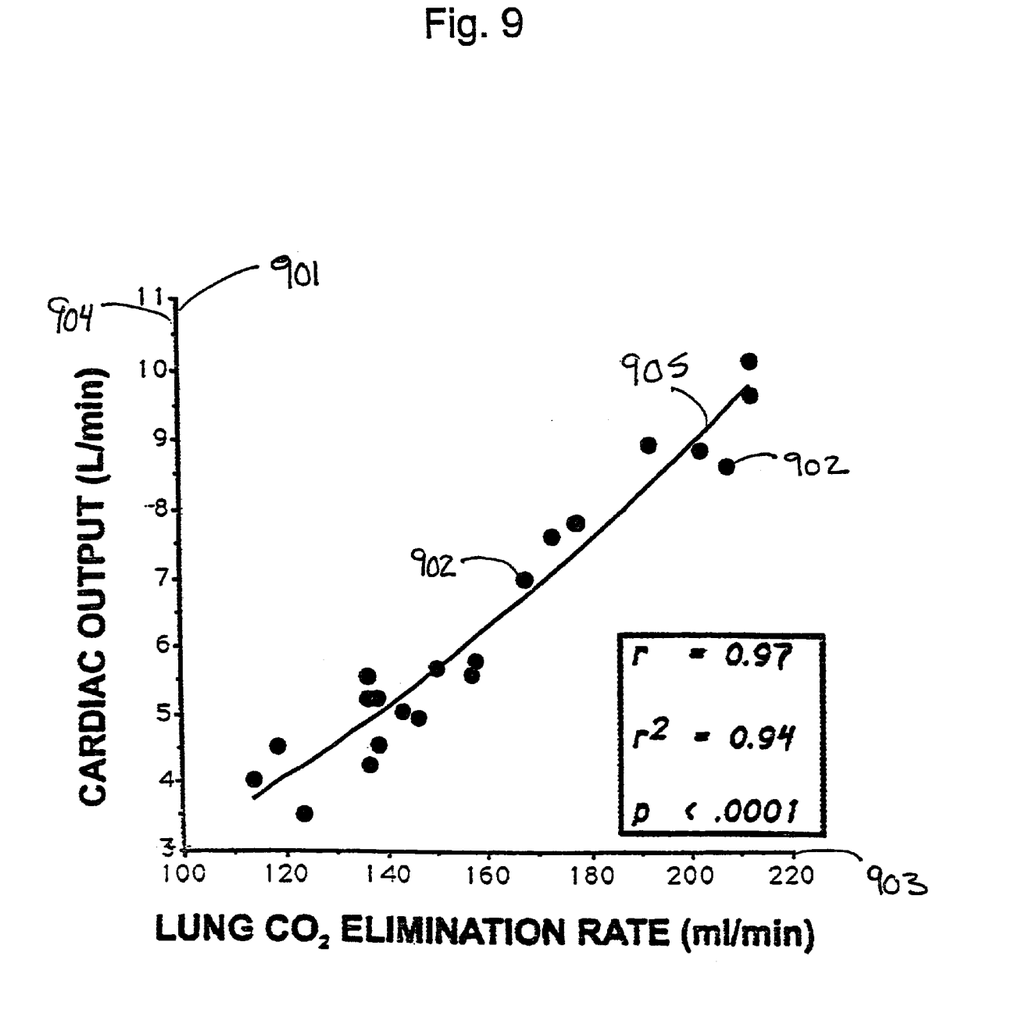
FIG. 9 is a lung carbon dioxide elimination rate-cardiac output curve illustrating the correlation between lung carbon dioxide elimination rate and cardiac output for a healthy patient.

Similarly, referring now to the experimental plot 901 illustrated in FIG. 9, the experimental data points 902 representative of the twenty-one measurements taken on the patients with normal ventilation-to-perfusion relationships, using lung carbon dioxide elimination rates derived from single breath analysis taken over a one minute time interval of patient respiration, are shown against an x-axis 903 representative of lung carbon dioxide elimination rate (ml/min) and a y-axis 904 representative of cardiac output (L/min). Statistical analysis yielded curve 905 having the constant values for a second predictive relationship for healthy patients of:

a=0.411;

b=0.013; and c=0.001403.

Referring to FIGS. 8 and 9, the positive and significant correlation between $LCO_2$ and CO (r=0.95 for patients with abnormal ventilation-to-perfusion relationships and r=0.97 for patients with normal ventilation-to-perfusion relationships) indicated that the current value of the carbon dioxide elimination rate from the flow rate and the percentage of carbon dioxide present in the gas expired by the patient is a good predictor of cardiac output ($r^2=0.90$ for patients with abnormal ventilation-to-perfusion relationships and $r^2=0.94$ for patients with normal ventilationto-perfusion relationships).

Another predictive equation, giving almost as good a predictive equation for patients with normal ventilation-to-perfusion relationships is in the form of the following linear predictive relationship:

$$CO = d(LCO_2) - e$$

where CO is the cardiac output of the patient in L/min, $LCO_2$ is the current value of the lung carbon dioxide elimination rate of the patient in ml/min, and d and e are constants, the value of which depend upon the experimental data. For example, referring again to FIG. 8, the eleven measurements taken on the patients with normal ventilation-to-perfusion relationships, using lung carbon dioxide elimination rates derived from single breath analysis taken over a one minute time interval of patient respiration, yielded the constant values for the alternative predictive relationship for healthy patients of:

d=0.0603; and e=3.36.

It must be emphasized that the above equations are merely exemplary and represent the best correlations/predictions obtained by linear regression analysis on a limited set of measurements. The measurements were not made under optimal research conditions and no attempt was made to select the best data or to determine the reason for readings that departed significantly from the average value. In addition to obtaining larger and more carefully controlled data samples, it is probable that the predictive equations could be further improved by using more sophisticated analysis, such as multiple or geometric regression instead of linear regression techniques.

The above results demonstrate, however, that the determination of the lung carbon dioxide elimination rate of the patient 10 may provide a simple and easy method for predicting a measured level of the cardiac output of a living being by noninvasive means.

One embodiment of the present invention may be used on ill patient's with an abnormal ventilation-to-perfusion relationship while an alternate embodiment may be used on healthy patient's with a normal ventilation-to-perfusion relationship. In either of these embodiments, the input device 50 is not required, as the predictive relationship for either the ill or the healthy patient respectively, which as noted above differ slightly, would be the only predictive relationship retained in the memory 42 of the processor 40 for correlating the current value of the carbon dioxide elimination rate to the cardiac output level of the patient. Therefore, the appropriate cardiac ouput level would be displayed to the operator upon the application of the correct embodiment to the patient, i.e., the "ill patient" embodiment, having the first predictive relationship, being attached to the ill patient or the "healthy patient" embodiment, having the second predictive relationship, being attached to the healthy patient.

However, as shown in FIG. 7, the preferred embodiment of the present invention would contain both the first and second predictive relationships in the processor memory 42 for correlating the lung carbon dioxide elimination rate to the cardiac output level of the patient. This embodiment is preferred as it allows more universal application of the method and system of the present invention. In Block 704, for this embodiment, prior to initiating any correlation of the cardiac output level, the processor 40 must be instructed as to which predictive equation to select. This selection, to which the processor 40 is responsive by selecting and using, in Block 705, the selected predictive equation to correlate the cardiac output level of the patient 10, may be made by the operator by input to the processor 40 via the input device 50 or, by the selection of a "ill/healthy" selection switch [not shown], which transmits a selecting signal to the processor 40 indicative of the patient's status, or by any suitable selecting device. The important requirement is that the appropriate first or second predictive relationship be utilized depending upon the patient's relative health status.

Although the present invention has been described with reference to specific detail of certain embodiments thereof, it is not intended that such details should be regarding as limitations upon the scope of the invention except as and to the extent that they are included in the accompanying claims.

What is claimed is:

1. A method for determining a cardiac output level of a patient, the method comprising:
   (a) monitoring the carbon dioxide production of the patient to obtain a current value of the lung carbon dioxide elimination rate of the patient; and
   (b) predicting the cardiac output level of the patient as a function of the current value of the carbon dioxide elimination rate, wherein the cardiac output level of the patient predictively increases as the lung carbon dioxide rate increases.

2. The method of claim 1, wherein the monitoring step comprises the steps of:
   (i) sensing a flow rate of the exhaled gas expired by the patient and generating a flow signal representative of the flow rate;
   (ii) sensing a carbon dioxide level of the exhaled gas expired by the patient and generating a carbon dioxide signal representative of the carbon dioxide level; and
   (iii) processing the flow signal and the carbon dioxide signal to determine the current value of the lung carbon dioxide elimination rate of the patient.

3. The method of claim 2, wherein the flow rate sensing step comprises continuously measuring the flow rate of exhaled gas during an exhalation effort by the patient.

4. The method of claim 2, wherein the carbon dioxide level sensing step comprises continuously sensing the carbon dioxide level of the exhaled gas during an exhalation effort by the patient.

5. The method of claim 2, wherein the step of generating the flow signal further comprises the step of converting the flow signal to a digitized flow signal.

6. The method of claim 2, wherein the step of generating the carbon dioxide signal further comprises the step of converting the carbon dioxide signal to a digitized carbon dioxide signal.

7. The method of claim 2, wherein the step of processing comprises the steps of:
   (A) extracting a measured exhaled volume of the exhaled gas from the flow signal;
   (B) storing a set of curve data representative of the sensed carbon dioxide level of the exhaled breathing gas as a function of the measured exhaled volume of the gas; and
   (C) integrating the set of curve data over a time interval to determine the current value of the lung carbon dioxide elimination rate of the patient.

8. The method of claim 7, wherein the time interval is one minute.

9. The method of claim 1, further comprising the step of displaying the cardiac output level.

10. The method of claim 9, wherein the step of displaying comprises the step of visually displaying the cardiac output level corresponding to the determined carbon dioxide elimination rate of the patient.

11. The method of claim 9, wherein the step of displaying comprises the step of recording the cardiac output level corresponding to the determined carbon dioxide elimination rate of the patient.

12. The method of claim 2, wherein the step of measuring the flow rate of the exhaled gas comprises measuring the flow rate of the exhaled gas in at least one location in a flow path of the exhaled gas.

13. The method of claim 2, wherein the step of sensing the carbon dioxide level of the exhaled gas comprises sensing the carbon dioxide level of the exhaled gas in at least one location in a flow path of the exhaled gas.

14. The method of claim 2, further comprising providing the patient with a breathing attachment having a proximal end, a distal end, and a breathing channel extending therethrough from the proximal end to the distal end, the distal end of the breathing attachment in flow communication with the lungs of the patient such that a flow path of the exhaled gas passes through the breathing channel, wherein the step of measuring the flow rate of the exhaled gas comprises measuring the flow rate of the exhaled gas in the flow path of the exhaled gas near the proximal end of the breathing attachment, and wherein the step of sensing the carbon dioxide level of the exhaled gas comprises sensing the carbon dioxide level of the exhaled gas in the flow path of the exhaled gas near the proximal end of the breathing attachment.

15. The method of claim 1, wherein the step of predicting comprises the steps of:

(i) selecting the predictive relationship appropriate for the patient, wherein a first predictive relationship is selected for ill patients and a second predictive relationship is selected for healthy patients; and (ii) determining the cardiac output level based on the selected predictive relationship and the current value of the lung carbon dioxide elimination rate of the patient.

16. A system for determining a cardiac output level of a patient, comprising:

means for monitoring the lung carbon dioxide elimination rate of the patient which is representative of the volume of carbon dioxide expired by the patient per unit time;

processing means responsive to the carbon dioxide elimination rate monitoring means for determining a current value for the carbon dioxide elimination rate of the patient; and predicting means for determining the cardiac output level of the patient based on the determined current value of the current value of the carbon dioxide elimination rate, wherein the cardiac output level of the patient predictively increases as the lung carbon dioxide elimination rate of the patient increases.

17. The system of claim 16, wherein the monitoring means is comprised of means for sensing the flow rate of the exhaled gas expired by the patient and means for sensing the carbon dioxide level of the exhaled gas expired by the patient.

18. The system of claim 17, wherein the processing means includes means responsive to the flow rate sensed by the flow rate sensing means for providing the measured volume of the exhaled gas expired by the patient during an exhalation effort of the patient.

19. The system of claim 18, wherein said processing means is responsive to the measured volume of the exhaled gas and the carbon dioxide level sensed by the carbon dioxide sensing means for determining the current value of the carbon dioxide elimination rate of the patient.

20. The system of claim 17, wherein the flow rate sensing means and the carbon dioxide sensing means are disposed in a flow path of the exhaled gas.

21. The system of claim 20, further comprising a breathing attachment having a proximal end, a distal end, and a breathing channel extending therethrough from the proximal end to the distal end, the distal end of the breathing attachment in flow communication with the lungs of the patient such that the flow path of the exhaled gas passes through the breathing channel, wherein the flow rate measuring means and the carbon dioxide sensing means are disposed in the flow path of the exhaled gas near the proximal end of the breathing attachment.

22. The system of claim 16, further comprising display means, coupled to the predicting means, for displaying the measurement of the cardiac output level of the patient to an operator of the system.

23. The system of claim 16, wherein the predicting means includes means for selecting a predictive relationship appropriate for the patient, wherein a first predictive relationship is selected for ill patients and wherein a second predictive relationship is selected for healthy patients.

24. The system of claim 23, wherein the predicting means includes means for determining the cardiac output of the patient based on the selected predictive relationship and the determined current value of the carbon dioxide elimination rate.

25. The system of claim 16, further comprising storage means, coupled to the processing means and the predicting means, for storing the current value of the lung carbon dioxide elimination rate and the determined cardiac output level.

26. A system for determining a cardiac output level of a patient from the carbon dioxide elimination rate of the patient, the system comprising:

a flow rate sensor which measures a flow rate of the exhaled gas expired by the patient and which provides a flow signal representative of the flow rate;

a carbon dioxide sensor which senses a carbon dioxide level of the exhaled gas expired by the patient and which provides a carbon dioxide signal representative of the carbon dioxide level; and a processor which:
receives the carbon dioxide signal and the flow signal;
determines a current value of lung carbon dioxide elimination rate of the patient from the carbon dioxide signal and the flow signal; and
predicts the cardiac output level of the patient as a function of the current value of lung carbon dioxide elimination rate of the patient, wherein the cardiac output level of the patient predictively increases as the lung carbon dioxide elimination rate of the patient increases.

27. The system of claim 26, wherein the processor extracts a measured volume of exhaled gas from the flow signal and wherein the processor determines the current value of lung carbon dioxide elimination rate from the carbon dioxide signal and the measured volume.

28. The system of claim 26, further comprising a first digitizer which receives the flow signal from the flow rate sensor and converts the flow signal into a digitized flow signal which is received by the processor.

29. The system of claim 26, further comprising a second digitizer which receives the carbon dioxide signal and converts the carbon dioxide signal into a digitized carbon dioxide signal which is received by the processor.

30. The system of claim 26, wherein the flow rate sensor senses the flow of the exhaled gas continuously during an exhalation effort of the patient.

31. The system of claim 26, wherein the carbon dioxide sensor senses the carbon dioxide level of the exhaled gas continuously during the exhalation effort of the patient.

32. The system of claim 26, further comprising a display device which receives the cardiac output level from the processor and displays that level.

33. The system of claim 32, wherein the display device comprises a monitor which visually displays the cardiac output level.

34. The system of claim 32, wherein the display device is a recorder which records the cardiac output level.

35. The system of claim 26, wherein the flow rate sensor and the carbon dioxide sensor are disposed in a flow path of the gas expired by the patient.

36. The system of claim 35, further comprising a breathing attachment having a proximal end, a distal end, and a breathing channel extending therethrough from the proximal end to the distal end, the distal end of the breathing attachment in flow communication with the lungs of the patient such that the flow path of the exhaled gas passes through the breathing channel, wherein the flow rate measuring sensor and the carbon dioxide sensor means are disposed in the flow path of the exhaled gas near the proximal end of the breathing attachment.

37. The system of claim 35, wherein the carbon dioxide sensor is a capnometer.

38. The system of claim 35, wherein the flow rate measurement sensor is a pneumotachometer.

39. The system of claim 26, further comprising an input device operatively coupled to the processor.

40. The system of claim 39, wherein a first predictive relationship of the cardiac output level of the patient as a function of the current value of lung carbon dioxide elimination rate for ill patients may be selected by an operator via the input device, and wherein a second predictive relationship of the cardiac output level of the patient as a function of the current value of lung carbon dioxide elimination rate for for healthy patients may be selected by an operator via the input device, so that the processor uses the selected first or second predictive relationship to predict the cardiac output level of the patient based on the relative respiratory health of the patient.

41. A system for determining a cardiac output level of a patient from the carbon dioxide elimination rate of the patient, the system comprising:
  a flow rate measurement sensor which measures the flow rate of the exhaled gas expired by the patient and which provides a flow signal representative of that flow rate;
  a carbon dioxide sensor which senses the carbon dioxide level of the exhaled gas expired by the patient and which provides a carbon dioxide signal representative of that carbon dioxide level;
  a first processor which receives the carbon dioxide signal and the flow signal, and determines a current value of the lung carbon dioxide elimination rate of the patient from the carbon dioxide signal and the flow signal and which generates a lung carbon dioxide elimination rate signal representative of the current value of the lung carbon dioxide elimination rate; and
  a second processor which receives the lung carbon dioxide elimination rate signal and, based on the current value of that signal, predicts the cardiac output level of the patient, wherein the cardiac output level of the patient predictively increases as the lung carbon dioxide elimination rate of the patient increases.

42. The system of claim 41, wherein the flow rate sensor senses the flow of the exhaled gas continuously during an exhalation effort of the patient.

43. The system of claim 41, wherein the carbon dioxide sensor senses the carbon dioxide level of the exhaled gas continuously during the exhalation effort.

44. The system of claim 41, further comprising a display device which receives the cardiac output level from the second processor and displays that level.

45. The system of claim 41, wherein the flow rate sensor and the carbon dioxide sensor are disposed in a flow path of the gas expired by the patient.

46. The method of claim 45, further comprising a breathing attachment having a proximal end, a distal end, and a breathing channel extending therethrough from the proximal end to the distal end, the distal end of the breathing attachment in flow communication with the lungs of the patient such that the flow path of the exhaled gas passes through the breathing channel, wherein the flow rate measuring sensor and the carbon dioxide sensor are disposed in the flow path of the exhaled gas near the proximal end of the breathing attachment.

47. The system of claim 41, further comprising an input device operatively coupled to the second processor.

48. The system of claim 47, wherein a predictive relationship of the cardiac output level of the patient as a function of the current value of lung carbon dioxide elimination rate may be selected by an operator via the input device, wherein a first predictive relationship is selected for ill patients and a second predictive relationship is selected for healthy patients so that the second processor predicts the cardiac output level based on the relative respiratory health of the patient.

49. A method for determining a cardiac output level of a patient, the method comprising:
  (a) monitoring the carbon dioxide production of the patient to obtain a current value of the lung carbon dioxide elimination rate of the patient by:
    (i) sensing a flow rate of the exhaled gas expired by the patient and generating a flow signal representative of the flow rate;
    (ii) sensing a carbon dioxide level of the exhaled gas expired by the patient and generating a carbon dioxide signal representative of the carbon dioxide level; and
    (iii) processing the flow signal and the carbon dioxide signal to determine the current value of the lung carbon dioxide elimination rate of the patient by:
      (A) extracting a measured exhaled volume of the exhaled gas from the flow signal;
      (B) storing a set of curve data representative of the sensed carbon dioxide level of the exhaled breathing gas as a function of the measured exhaled volume of the gas; and
      (C) integrating the set of curve data over a time interval to determine the current value of the lung carbon dioxide elimination rate of the patient; and
  (b) predicting the cardiac output level of the patient as a function of the current value of the carbon dioxide elimination rate, wherein the cardiac output level of the patient predictively increases as the lung carbon dioxide rate increases.

50. The method of 49, wherein the time interval is one minute.

51. A method for determining a cardiac output level of a patient, the method comprising:
  (a) monitoring the carbon dioxide production of the patient to obtain a current value of the lung carbon dioxide elimination rate of the patient; and
  (b) predicting the cardiac output level of the patient as a function of the current value of the carbon dioxide elimination rate by:
    (i) selecting the predictive relationship appropriate for the patient, wherein a first predictive relationship is selected for ill patients and a second predictive relationship is selected for healthy patients; and
    (ii) determining the cardiac output level based on the selected predictive relationship and the current value of the lung carbon dioxide elimination rate of the patient,
wherein the cardiac output level of the patient predictively increases as the lung carbon dioxide rate increases.

52. A system for determining a cardiac output level of a patient, comprising:
  means for monitoring the lung carbon dioxide elimination rate of the patient which is representative of the volume of carbon dioxide expired by the patient per unit time;
  processing means responsive to the carbon dioxide elimination rate monitoring means for determining a current value for the carbon dioxide elimination rate of the patient; and
  predicting means for determining the cardiac output level of the patient based on the determined current value of the current value of the carbon dioxide elimination rate, the predicting means including means for selecting a predictive relationship appropriate for the patient, wherein a first predictive relationship is selected for ill patients and wherein a second predictive relationship is selected for healthy patients, and wherein the cardiac output level of the patient predictively increases as the lung carbon dioxide elimination rate of the patient increases.

53. The system of claim 52, wherein the predicting means includes means for determining the cardiac output of the patient based on the selected predictive relationship and the determined current value of the carbon dioxide elimination rate.

54. A system for determining a cardiac output level of a patient from the carbon dioxide elimination rate of the patient, the system comprising:

a flow rate sensor which measures a flow rate of the exhaled gas expired by the patient and which provides a flow signal representative of the flow rate;

a carbon dioxide sensor which senses a carbon dioxide level of the exhaled gas expired by the patient and which provides a carbon dioxide signal representative of the carbon dioxide level;

an input device;

a processor, operatively coupled to the input device, which:

receives the carbon dioxide signal and the flow signal;

determines a current value of lung carbon dioxide elimination rate of the patient from the carbon dioxide signal and the flow signal; and predicts the cardiac output level of the patient as a function of the current value of lung carbon dioxide elimination rate of the patient, wherein the cardiac output level of the patient predictively increases as the lung carbon dioxide elimination rate of the patient increases, wherein a first predictive relationship of the cardiac output level of the patient as a function of the current value of lung carbon dioxide elimination rate for ill patients may be selected by an operator via the input device, and wherein a second predictive relationship of the cardiac output level of the patient as a function of the current value of lung carbon dioxide elimination rate for for healthy patients may be selected by an operator via the input device, so that the processor uses the selected first or second predictive relationship to predict the cardiac output level of the patient based on the relative respiratory health of the patient.

55. A system for determining a cardiac output level of a patient from the carbon dioxide elimination rate of the patient, the system comprising:

a flow rate measurement sensor which measures the flow rate of the exhaled gas expired by the patient and which provides a flow signal representative of that flow rate;

a carbon dioxide sensor which senses the carbon dioxide level of the exhaled gas expired by the patient and which provides a carbon dioxide signal representative of that carbon dioxide level;

an input device;

a first processor which receives the carbon dioxide signal and the flow signal, and determines a current value of the lung carbon dioxide elimination rate of the patient from the carbon dioxide signal and the flow signal and which generates a lung carbon dioxide elimination rate signal representative of the current value of the lung carbon dioxide elimination rate; and a second processor, operatively coupled to the input device, which receives the lung carbon dioxide elimination rate signal and, based on the current value of that signal, predicts the cardiac output level of the patient, wherein the cardiac output level of the patient predictively increases as the lung carbon dioxide elimination rate of the patient increases, and wherein a predictive relationship of the cardiac output level of the patient as a function of the current value of lung carbon dioxide elimination rate may be selected by an operator via the input device, wherein a first predictive relationship is selected for ill patients and a second predictive relationship is selected for healthy patients, so that the second processor predicts the cardiac output level based on the relative respiratory health of the patient.

* * * * *